(12) United States Patent
Draper et al.

(10) Patent No.: US 10,695,502 B2
(45) Date of Patent: *Jun. 30, 2020

(54) DRIVE MECHANISM OF A DRUG DELIVERY DEVICE COMPRISING AN ACCESSORY DRIVE

(71) Applicant: Sanofi-Aventis Deutschland GMBH, Frankfurt am Main (DE)

(72) Inventors: Paul Richard Draper, Worcestershire (GB); Anthony Paul Morris, West Midlands (GB); Stephen Francis Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/168,788

(22) Filed: Oct. 23, 2018

(65) Prior Publication Data

US 2019/0083713 A1 Mar. 21, 2019

Related U.S. Application Data

(63) Continuation of application No. 14/760,432, filed as application No. PCT/EP2014/050544 on Jan. 14, 2014, now Pat. No. 10,112,016.

(30) Foreign Application Priority Data

Jan. 14, 2013 (EP) ..................................... 13151199

(51) Int. Cl.
*A61M 5/31* (2006.01)
*A61M 5/315* (2006.01)
*A61M 5/20* (2006.01)

(52) U.S. Cl.
CPC .......... *A61M 5/31551* (2013.01); *A61M 5/20* (2013.01); *A61M 5/31585* (2013.01);
(Continued)

(58) Field of Classification Search
CPC .... A61M 2005/2026; A61M 2205/332; A61M 5/20; A61M 5/31551; A61M 5/31585
See application file for complete search history.

(56) References Cited

U.S. PATENT DOCUMENTS

2011/0306939 A1 12/2011 Harms
2012/0259285 A1 10/2012 Schabbach

FOREIGN PATENT DOCUMENTS

EP 2266647 12/2010
JP H11-267207 10/1999
(Continued)

OTHER PUBLICATIONS

International Search Report and Written Opinion in Application No. PCT/EP2014/050544, dated Apr. 4, 2014, 10 pages.
(Continued)

*Primary Examiner* — Imani N Hayman
(74) *Attorney, Agent, or Firm* — Fish & Richardson P.C.

(57) ABSTRACT

A drive mechanism of a drug delivery device and a respective drug delivery device for setting and dispensing of a dose of a medicament are presented, where the drive mechanism has an elongated housing extending in an axial direction, a piston rod to operably engage with a piston of a cartridge containing the medicament, a dosing arrangement manually and axially displaceable relative to the housing for setting and dispensing of the dose, and an accessory drive operably engaged with the piston rod to support a manually operated dose dispensing displacement of the dosing arrangement.

17 Claims, 5 Drawing Sheets

(52) U.S. Cl.
CPC ............... *A61M 2005/2026* (2013.01); *A61M 2205/332* (2013.01)

(56) References Cited

FOREIGN PATENT DOCUMENTS

| | | |
|---|---|---|
| JP | 2000-513973 | 10/2000 |
| JP | 2002-503122 | 1/2002 |
| JP | 2002-543931 | 12/2002 |
| JP | 2003-516193 | 5/2003 |
| JP | 2010-509984 | 4/2010 |
| JP | 2011-156493 | 8/2011 |
| JP | 2012-504992 | 3/2012 |
| JP | 2012/127046 | 7/2012 |
| JP | 2012-530576 | 12/2012 |
| WO | WO 98/01168 | 1/1998 |
| WO | WO 98/56439 | 12/1998 |
| WO | WO 00/69488 | 11/2000 |
| WO | WO 01/41838 | 6/2001 |
| WO | WO 2006/039930 | 4/2006 |
| WO | WO 2010/043533 | 4/2010 |
| WO | WO 2010/056367 | 5/2010 |
| WO | WO 2010/149717 | 12/2010 |
| WO | WO 2012/127046 | 9/2012 |
| WO | WO 2012/130901 | 10/2012 |

OTHER PUBLICATIONS

International Preliminary Report on Patentability in Application No. PCT/EP2014/050544, dated Jul. 14, 2015, 7 pages.

DRIVE MECHANISM OF A DRUG DELIVERY DEVICE COMPRISING AN ACCESSORY DRIVE

CROSS REFERENCE TO RELATED APPLICATIONS

The present application is a continuation of U.S. patent application Ser. No. 14/760,432, filed Jul. 10, 2015, now U.S. Pat. No. 10,112,016, issued on Oct. 30, 2018, which is a U.S. National Phase Application pursuant to 35 U.S.C. § 371 of International Application No. PCT/EP2014/050544, filed Jan. 14, 2014, which claims priority to European Patent Application No. 13151199.0, filed Jan. 14, 2013. The entire contents of each of these applications are incorporated by reference herein.

TECHNICAL FIELD

The present invention relates to a drive mechanism of a drug delivery device to dispense and/or to inject a predefined dose of a medicament from a cartridge. The drug delivery device is generally manually operable and allows for individually setting and/or dispensing of a dose of the medicament.

BACKGROUND

User operated drug delivery devices are as such known in the art. They are typically applicable in circumstances, in which persons without formal medical training, i.e., patients, need to administer an accurate and predefined dose of a medicament, such as heparin or insulin. In particular, such devices have application, where a medicament is administered on a regular or irregular basis over a short-term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose.

Some mechanically implemented drug delivery devices, e.g. pen-type injectors, comprise a dosing or dose setting arrangement featuring a dose setting member to be displaced in axial proximal direction for setting of a dose. For dispensing of a respective dose, the proximally extended dose setting member may then have to be manually depressed in distal direction, e.g. to advance a piston of the cartridge in distal direction. Here, a user may have to exert a comparatively large dispensing force, which may pose a burden to physically impaired persons or patients.

Apart from manually or purely mechanically operated drug delivery devices there also exist electro-mechanical drug delivery devices wherein at least dose setting, dose selection or administration of an appropriate dose of the medicament is controlled by way of electronic circuitry, for example a controller, a microprocessor, and/or the like. Such electronic or electro-mechanical devices provide a high dosing accuracy and may support long-term monitoring of doses dispensed by the device. Hence, a dosing and dispensing scheme can even be stored in the device allowing to recall the dose dispensing history later on.

However, with electronic or electro-mechanical devices, setting and dispensing of a dose might be less intuitive compared to an all-mechanically implemented device. In particular, with a mechanically implemented device, the user has to apply a certain injection force, thereby obtaining a force feedback. By introducing an electro-mechanical device to the patient and replacing an all-mechanical device, the patient or user may be confronted with an unfamiliar or inconvenient operation scheme. Hence, there may emerge a certain danger of misuse and suboptimal medical treatment. Also, the acceptance of such an electro-mechanical device by the user may be rather low.

With an electronic or electromechanical drug delivery device not only the dose setting and dose dispensing process is electrically implemented. Also a dose indicator, typically in form of a display to visually illustrate the size of a dose to the user may be implemented all electronically. However, in the event that the drug delivery device or one of its electronic components becomes subject to failure, there may be a certain danger, that the dose is incorrectly or incompletely indicated to the user of the device. It may then occur that the indicated or illustrated dose size does not match with the size of a dose actually set or dispensed by the drug delivery device.

It is therefore an object of the present invention to provide an improved drive mechanism for a drug delivery device, in particular for a pen-type injector. The drive mechanism should be mechanically operable and should provide direct and intuitive feedback to the user during dose dispensing. The drive mechanism should further come along with a substantially reduced dispensing force required to be exerted by the user for dose injecting or dose dispensing. In that sense the drive mechanism should provide a rather easy and intuitive handling, both for setting as well as for dispensing of a dose. Moreover, the invention also relates to a drug delivery device comprising such improved drive mechanism.

SUMMARY

In a first aspect a drive mechanism of a drug delivery device is provided. The drive mechanism is operable for setting as well as for dispensing of a dose of a medicament. The drive mechanism comprises an elongated housing extending in an axial direction. The drive mechanism further comprises a piston rod to operably engage with a piston of a cartridge, wherein the cartridge contains the medicament to be dispensed by the drive mechanism and/or by the drug delivery device, respectively.

Typically, the cartridge comprises a piston slidably disposed therein in axial direction that serves as a proximal seal of the cartridge's body or barrel. The drive mechanism is particularly operable to apply or to exert distally-directed thrust to the piston of the cartridge in order to expel a required dose of the medicament via a distally located septum of the cartridge, which is to be penetrated by a piercing element, such like an injection needle.

The drive mechanism further comprises a dosing arrangement manually and axially displaceable relative to the housing for setting and for dispensing of the dose. By means of the dosing arrangement, a size of a dose to be dispensed by the device can be individually set by the user during a dose setting procedure. In a subsequent step and after setting of a predefined dose, the user may then trigger or conduct an injection procedure by way of manually applying an injection force in distal direction to the dosing arrangement, in particular to a dose dispensing member, which may be connected with or may be implemented in the dosing arrangement.

Here the dosing arrangement may allow and support setting of doses of variable size. Alternatively, the dosing arrangement may be configured to dispense a fixed dose, which is not to be modified by the user.

The drive mechanism further comprises an accessory or auxiliary drive operably engaged with the piston rod of the drive mechanism to support the manually operated dose dispensing displacement of the dosing arrangement. By means of the accessory drive, the dispensing procedure can be supported. The accessory drive typically provides an additional force or torque by way of which a manually operable dose dispensing action can be supported. Consequently, the minimum dispensing force to be provided and to be exerted by a user can be effectively reduced. The general handling of the drive mechanism and of a respective drug delivery device can therefore be enhanced and facilitated.

The accessory or auxiliary drive is particularly adapted to exclusively support the dispensing action of the drive mechanism. During dose setting, the accessory drive may be effectively inoperable. Moreover, the accessory drive is operable to exclusively support but not to entirely control a dispensing procedure of the drive mechanism. In this way, the mechanical interaction between the dosing arrangement and the piston rod can remain substantially unmodified compared to an all mechanical implementation of a drive mechanism.

Typically, the dosing arrangement is subject to an axially-directed displacement relative to the housing during dose setting as well as during dose dispensing. Since the dosing arrangement and the piston rod remain operably and mechanically engaged, overall handling of the dosing arrangement for setting and/or dispensing of a dose may strongly resemble a general handling of an all mechanically implemented drive mechanism, to which a user or patient may already be used to.

Moreover, through the mechanical and operable engagement of dosing arrangement and piston rod the drive mechanism provides an all mechanical indication and control about the size of the dose actually set and/or dispensed. In the event, that the accessory drive should run out of power or in the event, that the accessory drive or components thereof become subject to malfunction, the drive mechanism remains fully operational. A malfunction of the accessory drive may then only affect the operational comfort of the drive mechanism and hence of the drug delivery device.

In another embodiment, the accessory drive is power operated. Here, the accessory drive is electrically driven. The accessory drive may therefore comprise a DC motor electrically connected to a battery, e.g. a rechargeable battery. Typically, the accessory drive is selectively operable on demand during a dose dispensing procedure. The accessory drive is activated at the beginning of a dispensing procedure and remains activated until the dispensing procedure ends.

The accessory drive typically provides a predefined torque of constant or variable magnitude which is to be transferred to at least one functional component of the drive mechanism to transfer the supplemental torque or driving force to the piston rod thereof. Mutual coupling of the accessory drive and the piston rod may either be permanent or temporal. Additionally, the mutual coupling of accessory drive and piston rod may comprise a clutch or a clutch mechanism, which is operable during dose dispensing to couple the accessory drive and the piston rod.

The mutual coupling of accessory drive and piston rod may comprise a direct mechanical interaction of the accessory drive with a rotatably supported piston rod. However, in the event, that the piston rod is rotatably locked to the housing and is to be slidingly displaced relative to the housing for dispensing of a dose, the accessory drive may be mechanically engaged with another functional component of the drive mechanism, e.g. with a drive sleeve or the like, which is either directly or indirectly engaged with the piston rod for driving the same in distal, hence in dose dispensing direction.

In a further embodiment the dosing arrangement comprises a dose setting member, a dose indicating member and a dose dispensing member. The dosing arrangement therefore represents and corresponds to a unit axially displaceably supported relative to the housing for setting and/or dispensing of a dose. In typical embodiments, the dose indicating member comprises a sleeve having various dose size indicating numbers printed thereon. The dose indicating member is displaceable in proximal direction relative to the housing during a dose setting procedure, thereby exhibiting a series of dose indicating numbers at its outer circumference.

Typically, such numbers show up in a dose indicating window of the housing. Furthermore, it is conceivable, that the housing comprises an indicator at its proximal end to visualize the size of a dose actually set by the drive mechanism.

The dose indicating member may comprise a dose setting member, e.g. at its proximal end. The dose setting member typically comprise a dose dial grip providing a well defined gripping and rotating of the dose setting member and the interconnected dose indicating member during a screw-like dose setting displacement of the entire dosing arrangement. At its proximal end face, the dosing arrangement may further comprise the dose dispensing member.

The dose dispensing member typically comprises a dose button to be depressed in distal direction for dispensing of a dose previously set during the dose setting procedure. Here, the dose dispensing member may also comprise a thrust-receiving structure to receive and to transfer distally-directed thrust exerted by a user's thumb during a dose dispensing procedure.

For switching the device from a dose setting mode into a dose dispensing mode, the dose dispensing member or the entire dosing arrangement may be displaceably supported in axial, typically in distal direction to activate or to deactivate a clutch mechanism of the drive mechanism. By activating or deactivating the clutch mechanism, the drive mechanism can be switched between a dispensing and a dose setting mode.

In a further embodiment, the accessory drive is operably engageable with the dose setting member or with the dose indicating member during a dose dispensing procedure for dispensing of the dose previously set. In this context an operable engagement between two or more components relates to a mechanical engagement for transferring a torque or a force effect between said components.

When mechanically and directly coupled to either the dose setting member or to the dose indicating member, a dispensing force provided by the accessory drive will be transferred via the dose setting member or via the dose indicating member to the piston rod.

Otherwise, the accessory drive may be directly coupled or engaged with the piston rod. Then, during a dispensing procedure supported by the accessory drive, the return motion of the dose setting member and/or of the dose indicating member may be governed and induced by the piston rod and/or by the user supported displacement of dose setting member.

In another embodiment, the dosing arrangement is axially displaceable in proximal direction relative to the housing for setting of the dose. Correspondingly, the dosing arrangement, hence the dose indicating member, the dose setting member as well as the dose dispensing member are displaceable in distal direction for dispensing of the dose. This way, the device may return into an initial configuration at the end of a dispensing procedure.

In another embodiment, the dose indicating member is operably, hence mechanically engaged with the piston rod during the dose dispensing procedure. In such an embodiment, the accessory drive may act on the dose indicating member and may be therefore operably and directly engaged with the dose indicating member. In this embodiment, activation of the accessory drive leads to a combined and supported displacement of the dose indicating member and of the piston rod during the dose dispensing procedure. Torque or forces provided by the accessory drive may then be transferred to the piston rod via the dose indicating member.

In this way, the dose metering and dose indicating can be implemented all-mechanically. A failure or malfunction of the software or electronic hardware of the drive mechanism has then no substantial effect on the dose metering and dose indication. As a consequence, the failure safety of the drive mechanism can be improved. As a further benefit, respective software and electronic hardware of the drive mechanism can be designed and implemented in a more simple and cost-efficient way.

In another embodiment, the dose dispensing member is operably, hence mechanically engaged with the piston rod during dose dispensing. In this way a manually applied and distally exerted dispensing force can be directly transferred to the piston rod for driving the same in distal direction. The combined and simultaneous displacement of the dose dispensing member and the piston rod can be supported by means of the accessory drive. For driving the piston rod in distal and dose dispensing direction during a dispensing procedure it may be sufficient when the accessory drive is operably or mechanically engaged with the dose dispensing member. A torque or force provided by the accessory drive can be transferred to the piston rod via the dose dispensing member, accordingly.

In another embodiment, the accessory drive is coupled with a switch to selectively activate and/or to deactivate the accessory drive. The switch may be inherently or automatically activated or deactivated at the beginning and/or at the end of a dose dispensing procedure, respectively. The switch may be particularly operable to start and to stop the accessory drive.

In a further embodiment, the switch is operably engaged with the dose dispensing member. In particular, the switch may be integrated into the dose dispensing member. In this way, depression of the dose dispensing member for dispensing of the dose may inherently and simultaneously depress the switch, thereby simultaneously activating the accessory drive.

In a further embodiment the switch is located in an interface between the dose dispensing member and the dose setting member. The switch may be implemented all-mechanically and may comprise a first portion fixed to the dispensing member and may further comprise a second portion fixed to the dose setting member. In this embodiment, the dose dispensing member is displaceable relative to the dose setting member, at least for dispensing of a dose. Relative displacement of the dose dispensing member with regard to the dose setting member may then lead to an electrical connecting or disconnecting of first and second portions of the switch, respectively.

According to another embodiment, the switch is actuatable against a restoring force. Typically, the switch is operable against the action of a restoring element, such like a spring element. Accordingly, depressing of the switch may take place against the action of the spring, such that a release of the switch automatically transfers the switch into its initial position under the action of the spring.

In a further embodiment, the drive mechanism comprises a control to regulate the power of the accessory drive in dependence of a dispensing force applied or exerted by a user of the drive. Here, the switch is operable to quantitatively determine the size or magnitude of a dispensing force acting thereon in distal direction during dose dispensing. By measuring or determining the magnitude of the externally applied force, the power of the accessory drive can be modified accordingly.

In the event that a user applies a comparatively large dispensing force to the dose dispensing member, the support of the accessory drive during a dose dispensing procedure may be comparatively small. In this case, electrical energy can be saved to a certain degree. In another event, wherein the actuation force provided by a user is comparatively low, the torque or force provided by the accessory drive may be raised accordingly.

In effect, the power and force or torque to be provided by the accessory drive can be individually adapted to the dispensing force exerted by a user and be actually present on the dose dispensing member. The magnitude of the power, force or torque provided by the accessory drive during dose dispensing can be regulated in such a way, that the sum of the forces applied by a user and the forces or torque provided by the accessory drive at least exceeds a predefined threshold force required to drive or to advance the piston rod in distal direction.

In another aspect the invention furthermore relates to a drug delivery device and in particular to a pen-type injector. The drug delivery device comprises a drive mechanism as described above and further comprises a cartridge at least partially filled with a medicament and being sealed by a piston in proximal direction, wherein the piston is to be displaced in distal direction by the piston rod of the drive mechanism for expelling and for dispensing of a dose of the medicament.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro37, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, an embodiment of the invention will be described by making reference to the drawings, in which.

DETAILED DESCRIPTION

Figure 1:
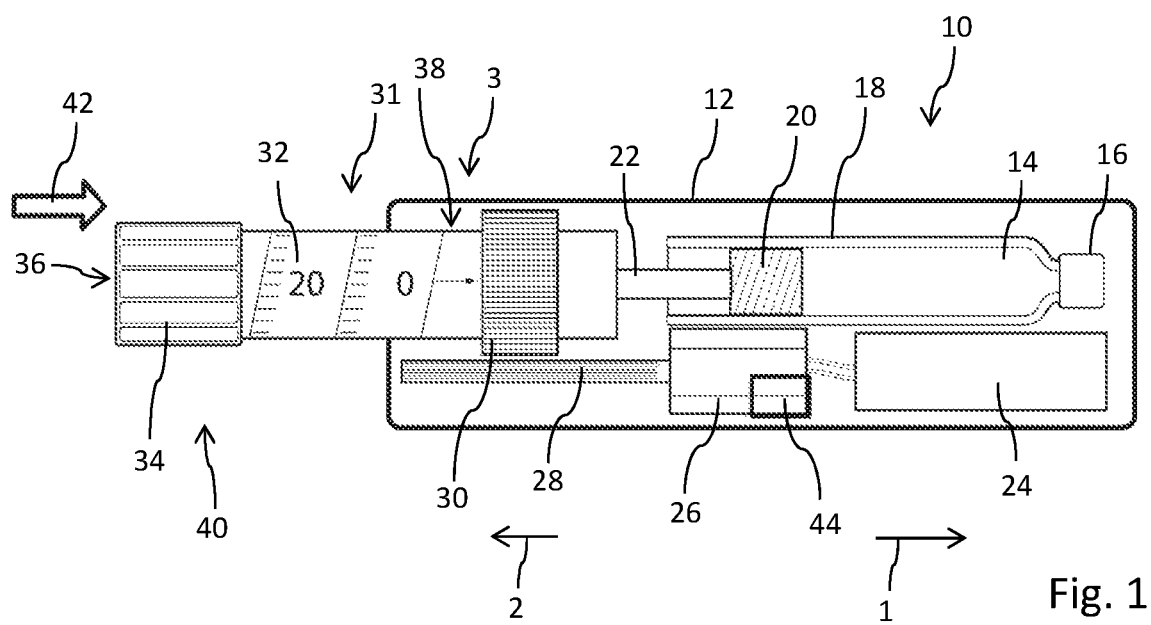
FIG. 1 schematically shows a first embodiment of a drive mechanism comprising an accessory drive.
Figure 2:
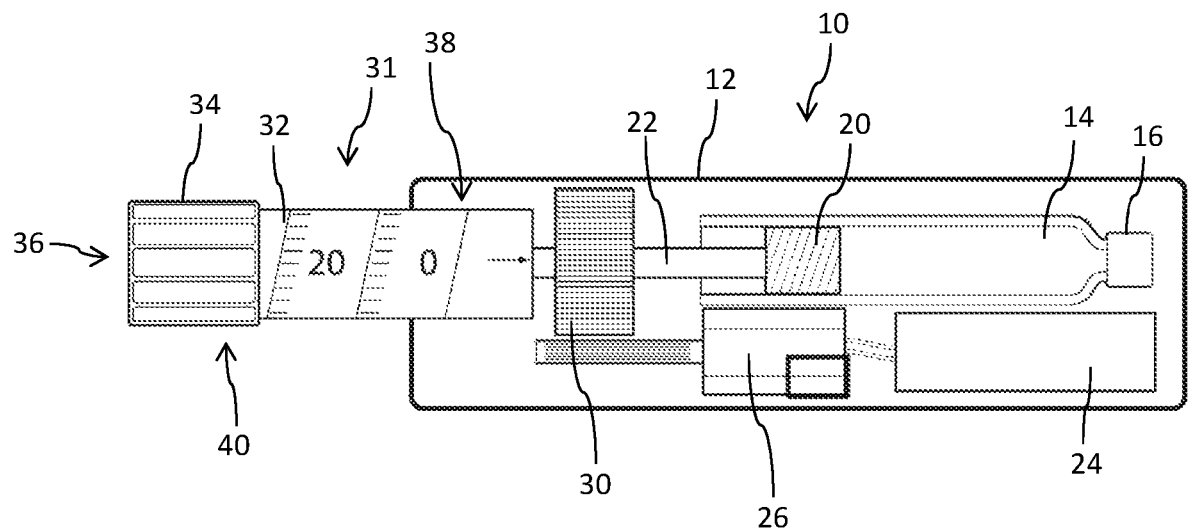
FIG. 2 shows another embodiment of the drive mechanism.

FIGS. 1 and 2 illustrate two different embodiments of an accessory drive 26 integrated in a drive mechanism 3 of a drug delivery device 10. As illustrated in FIGS. 1 and 2, the drug delivery device 10 and hence the drive mechanism 3 comprise a housing 12 to accommodate a cartridge 14 filled with a medicament to be dispensed by the drive mechanism 3. The cartridge 14 comprises a distally located seal 16, typically featuring a piercable septum to be penetrated by a double-tipped injection needle, which is not particularly illustrated here.

The cartridge 14 comprises a tubular-shaped barrel 18 which is sealed in proximal direction 2 by way of an axially displaceable piston 20. The drive mechanism 3 comprises at least a piston rod 22 to operably engage with the piston 20 of the cartridge 18. During a dispensing procedure, the piston rod 22 advances in distal direction 1 in order to exert pressure or thrust to the piston 20 for driving and advancing the same in distal direction 1. This way, a predefined amount of the medicament contained in the cartridge 14 can be expelled via the injection needle penetrating the proximal seal 16 of the cartridge 18.

The drive mechanism 3 comprises an accessory drive 26 electrically connected with a battery 24. The power operated accessory drive 26 is controllable via a control 44, by way of which the accessory drive 26 can be selectively activated or deactivated for supporting a dose dispensing procedure to be conducted by the drive mechanism 3. The accessory drive 26 is provided with a drive member or drive shaft 28, which, in the embodiment according to FIG. 1 is operably and directly engaged with a gear wheel 30 located on a dose indicating member 32 of a dosing arrangement 31 of the drive mechanism. The dose indicating member 32 comprises a dose indicating sleeve 32 featuring a series of numbers printed on its outer circumference, for indicating the size of a dose actually set by the dosing arrangement 31.

The dosing arrangement 31 comprises the sleeve-like dose indicating member 32 and a dose setting member 34, which may be implemented as a dose dial grip allowing a user to rotate the dose setting member 34 and the dose indicating member 32 in a screw-like motion for displacing the dosing arrangement 31 in proximal direction 2 relative to the housing 12, in particular for setting of a dose.

At its proximal end the dosing arrangement 31 comprises a dose dispensing member 36 which may be implemented as a dose button to receive a distally-directed dispensing force 42 exerted by e.g. a thumb of a user. During a dose dispensing procedure, the dosing arrangement 31 may return into an initial configuration. A corresponding distally-directed and user activated displacement of the entire dosing arrangement 31 relative to the housing 12 may come along with a respective counter-directed rotation of the dose indicating member 32 and/or of the dose setting member 34.

Typically, the drive mechanism 3 comprises a clutch mechanism 38, indicated in FIGS. 1 and 2, by way of which the drive mechanism 3 can be switched from the dose setting mode into the dose dispensing mode and vice versa. The clutch mechanism 38 is typically activated by depressing the dose button or dose dispensing member 36 in distal direction 1 at the beginning of a dose dispensing procedure.

The clutch 38 may be implemented in the dosing arrangement 31. It may provide an axially directed displacement between the dose setting member 34 and/or the dose dispensing member 36 relative to the dose indicating member 32, against the action of a spring force provided by a spring element.

In the interface between the dose dispensing member 36 and the dose setting member 34 or in the interface between the dose dispensing member 36 and the dose indicating member 32 a switch 40 is integrated as will be explained in greater detail with respect to FIGS. 3-11.

The switch 40 is electrically connected to the accessory drive 26, in particular to its control 44. Activation or deactivation of the switch 40 during a dose dispensing procedure will typically activate and deactivate the accessory drive 26 in order to support a dispensing action of the drive mechanism 3. As illustrated in FIG. 1, application of a distally-directed dispensing force 42, which is provided by a user of the device 10 may close or open the switch 40, thereby activating the accessory drive 26.

Under the action of both, the torque provided by the accessory drive 26 and by the force 42 provided by the user, the dosing arrangement 31 is operable to return into its initial configuration while applying a distally-directed advancing motion to the piston rod 22.

The accessory drive 26 may be dimensioned such that the torque to be provided via the drive member 28 is generally sufficient to move the piston rod 22 in distal direction 1. For dispensing of a dose it may be therefore sufficient just to apply a dispensing force 42 which is large enough to activate the switch 40 at the proximal end of the dosing arrangement 31.

Typically, the switch 40 is spring biased so that a premature release of the dose dispensing member 36 during a dose dispensing procedure immediately returns the switch 40 into an initial non-biased configuration, which is correlated with a deactivated accessory drive 26. As a consequence, release of the dose dispensing member 36 can be immediately transferred to a respective stop of the accessory drive.

In this way, the electrically- and/or power supported accessory drive 26 of the mechanism 3 provides a look and feel of an all-mechanically implemented drive mechanism 3. However, by means of the accessory drive 26, the magnitude of a dispensing force 42 required to trigger or to conduct a dispensing procedure can be effectively and advantageously reduced.

In the embodiment according to FIG. 1, the accessory drive 26 is directly engaged with the dose indicating member 32, e.g. in form of a dose sleeve of the drive mechanism 3. In this way, mechanical power provided by the accessory drive 26 is transferred to the piston rod 22 via the dose indicating member 32. In this embodiment, dose indicating member 32 and piston rod 22 remain coupled also during or for a dose dispensing procedure. Consequently, the axial position of the dose indicating member 32 is strictly correlated to the axial and actual position of the piston rod 22. By way of the mutual engagement of the dose indicating member 32 with the piston rod 22 the dose indicating member 32 always reflects the size of a dose actually dispensed by the drive mechanism 3.

In the embodiment according to FIG. 2, the accessory drive 26 is operably engaged with the piston rod 22. Hence, the gear wheel 30 that meshes measures with the drive member 28 of the accessory drive 26 is directly engaged with the piston rod 22. Here and in contrast to the embodiment according to FIG. 1, activation of the accessory drive 26 during a dose dispensing procedure may be without any effect to the configuration of the dosing arrangement 31.

Torque- or mechanical energy transmission between the accessory drive 26 and the piston rod 22 can be implemented in a rather direct way. Depending on the type of clutch mechanism 38 implemented between the dosing arrangement 31 and the piston rod 22 it is also conceivable with the embodiment according to FIG. 2, that the distally-directed and accessory drive supported displacement of the piston rod 22 is equally transferred to a corresponding distally directed displacement of the entire dosing arrangement 31.

The switch 40 as will be explained and illustrated in FIGS. 3-11 may feature a binary on/off functionality for activating or deactivating the accessory drive 26. In an alternative or additional embodiment it is also conceivable, that the switch 40 is implemented as a kind of a load cell or on the basis of at least one pressure sensitive member allowing to measure or to determine the magnitude of a force 42 exerted by a user of the device.

In this way, the power or driving force of the accessory drive 26 can be regulated accordingly. Here, the power of the accessory drive 26 can be individually and instantaneously adapted to the force 42 applied by a user for dose dispensing.

Figure 3:
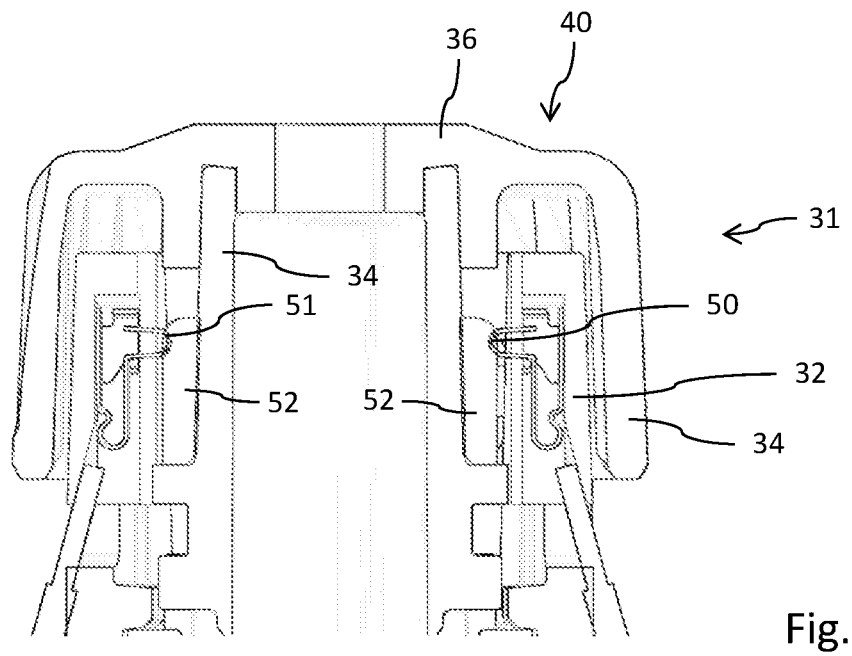
FIG. 3 is indicative of a switch implemented in the dosing arrangement in a first configuration.
Figure 4:
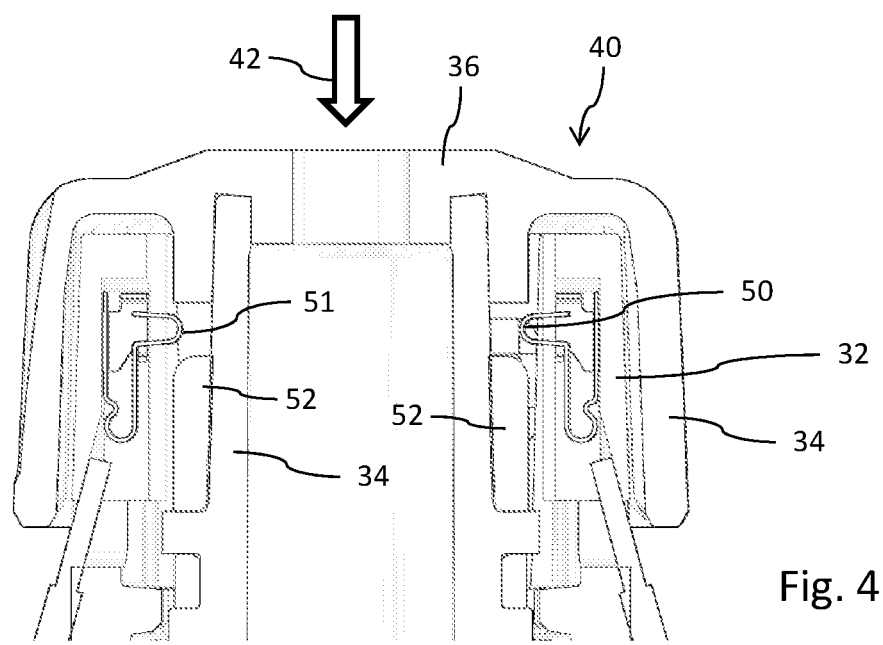
FIG. 4 shows the switch in a second configuration.

The cross-sectional illustration of FIG. 3 shows a proximal end of the dosing arrangement 31 during or after setting of a dose. For setting of a dose, the dose setting member 34 in form of a dose dial is to be rotated. As illustrated in FIG. 3, there are provided two radially inwardly extending spring-biased contact members 50, 51 at the inner circumference of the dose indicating member 32. In the configuration according to FIG. 3 the contact members 50, 51 are in mechanical contact with a circumferentially extending conductive ring 52 provided on an outer circumference of the dose setting member 34. By means of the conductive ring 52 an electrical contact between the oppositely located contact members 50, 51 can be established.

In the present embodiment, two contact members 50, 51 will deactivate the accessory drive 26 when in electrical contact with the conductive ring 52. Moreover, the dose setting member 34 and the dose dispensing member 36 are integrally formed. Hence, the dose dispensing member 36 forms a proximal end face of the dose dial or dose setting member 34.

Application of a distally-directed dispensing force 42 onto the dose setting member 34 or dose dispensing member 36 displaces the dose setting member 34 relative to the dose indicating member 32, which carries the two oppositely disposed contact members 50, 51. Since the conductive ring 52 is assembled to the dose setting member 34, the conductive ring 52 is axially and distally displaced relative to the two contact members 50, 51, thereby interrupting the electrical contact between the two contact members 50, 51.

Electrically disconnecting the two contact members 50, 51 then activates the accessory drive 26 via the control 44. At the same time, the relative axial displacement of dose setting member 34 and dose indicating member activates or deactivates the clutch, thereby mechanically switching the drive mechanism 3 into a dose dispensing mode.

The distally-directed displacement of the dose setting member 34 relative to the dose indicating member 32 and/or relative to the housing 12 typically occurs against the action of a spring, which is not explicitly illustrated here. As soon as the externally applied dispensing force 42 drops below a predefined threshold, said spring will serve to return the dose setting member 34 into its initial configuration as shown in FIG. 3, thereby closing the contact between the contact members 50, 51. As a consequence, the accessory drive 26 will then be deactivated.

Figure 5:
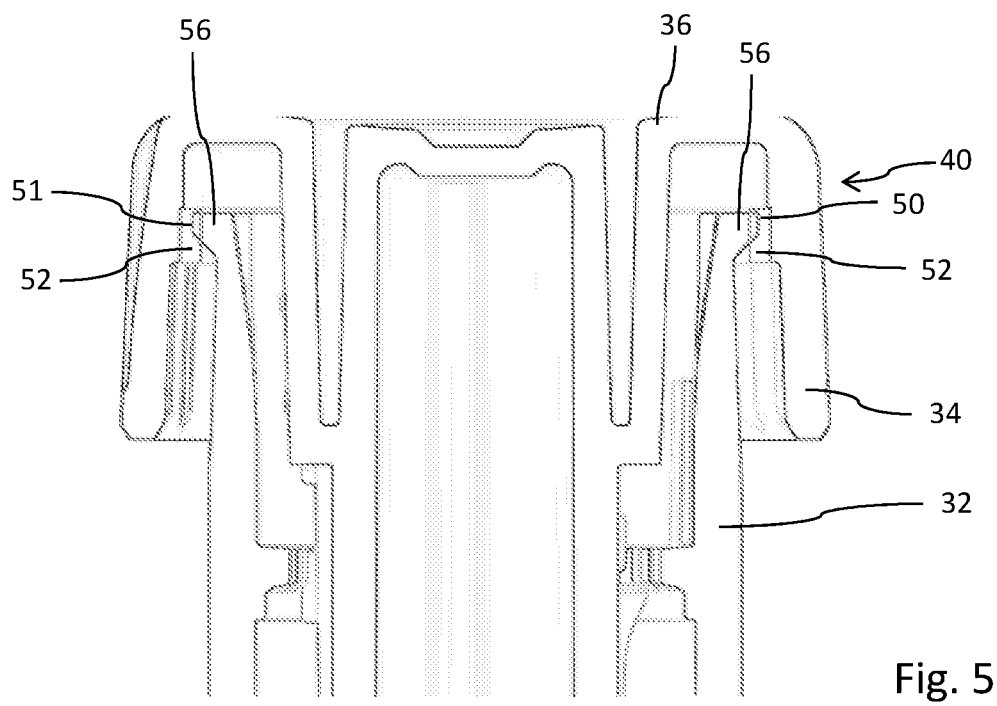
FIG. 5 shows another embodiment of a switch in a first configuration.
Figure 6:
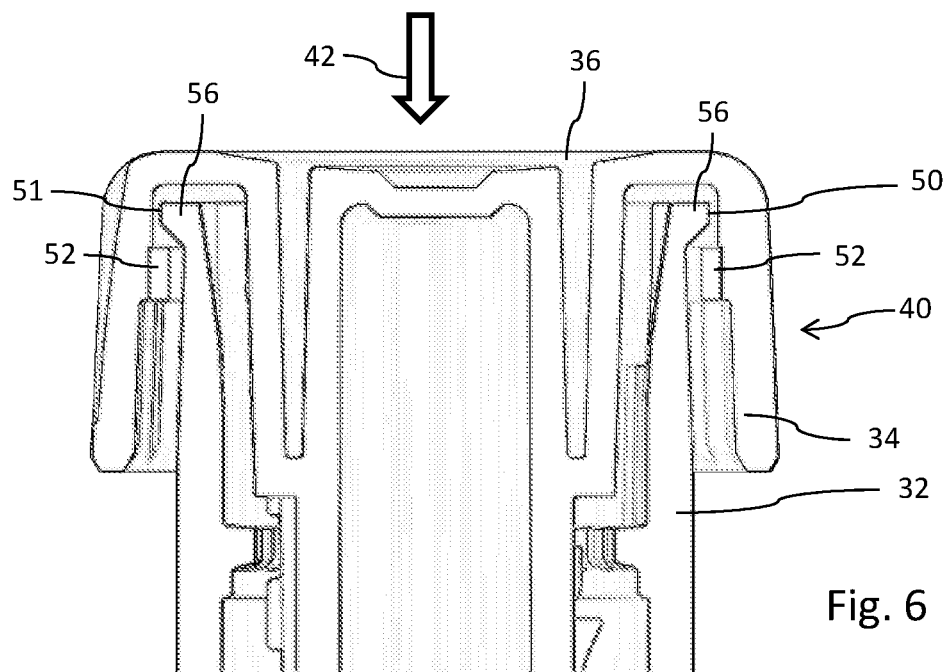
FIG. 6 shows the switch according to FIG. 5 in a second configuration.
Figure 7:
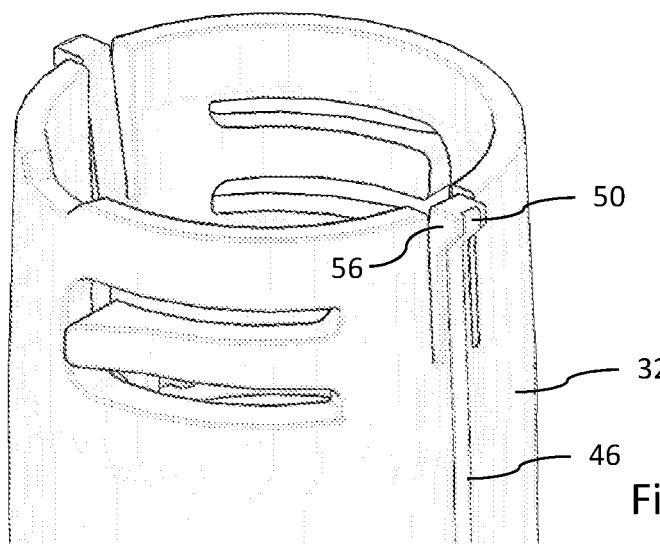
FIG. 7 is indicative of a proximal portion of the housing comprising a conductor path.

In another embodiment according to FIGS. 5-7, the switch 40 is implemented as a conductive ring 52 located at an inside wall portion of the dose setting member 34. As shown in FIGS. 5-7, the dose indicating member 32 in form of a dose indicating sleeve comprises radially outwardly extending and diametrically oppositely located protrusions 56 at a proximal end. The protrusions 56 are provided with conductor paths 46 extending in axial direction along the sleeve-like dose indicating member 32.

Also here, distally-directed displacement of the dose setting member 34 relative to the dose indicating member 32 against the action of a restoring spring brings the contact members 50, 51 out of engagement with the conductive ring 52. Consequently, and as already described in connection with the embodiment according to FIGS. 3 and 4, said disconnection may come along with an activation of the accessory drive 26.

Figure 8:
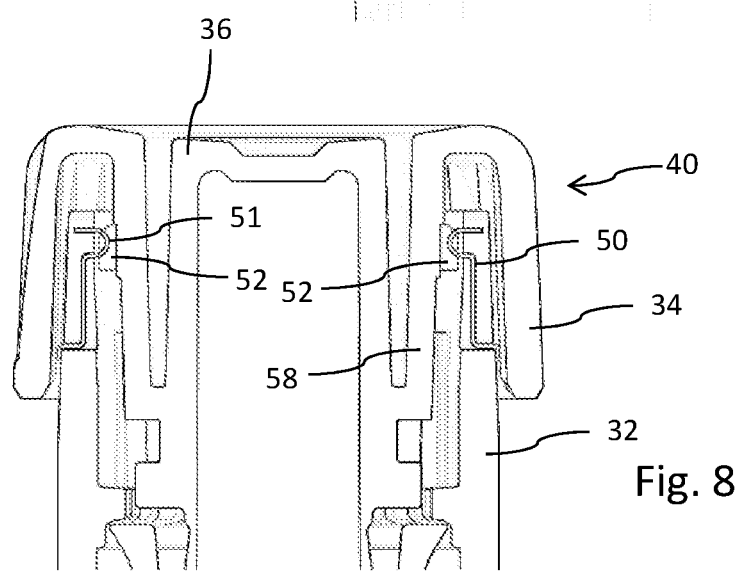
FIG. 8 shows another embodiment of the switch in a first configuration.
Figure 9:
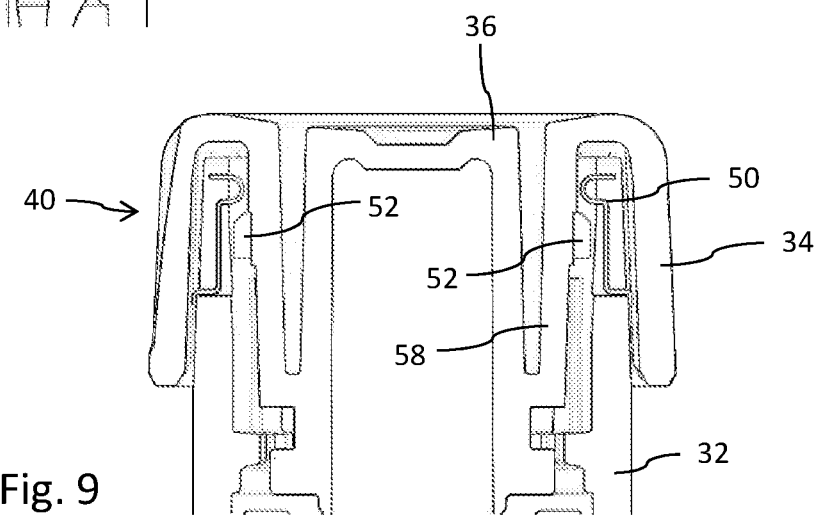
FIG. 9 is indicative of a second configuration of the switch according to FIG. 8.

In FIGS. 8 and 9 another embodiment is schematically illustrated, wherein the circumferentially extending conductive ring 52 is located and arranged on an inner sleeve portion 58 of the dose setting member 34 while oppositely located contact members 50, 51 are assembled and arranged at the proximal end of the dose indicating member 32. Here, the contact members 50, 51 are biased radially inwardly to mechanically engage with the conductive ring 52. As becomes apparent from a comparison of FIGS. 8 and 9, a distally-directed displacement of the dose setting member 34 relative to the dose indicating member 32 leads to an electrical disconnection of the two contact members 50, 51 with the same or with a similar effect on the accessory drive 26 as already explained above.

Figure 10:
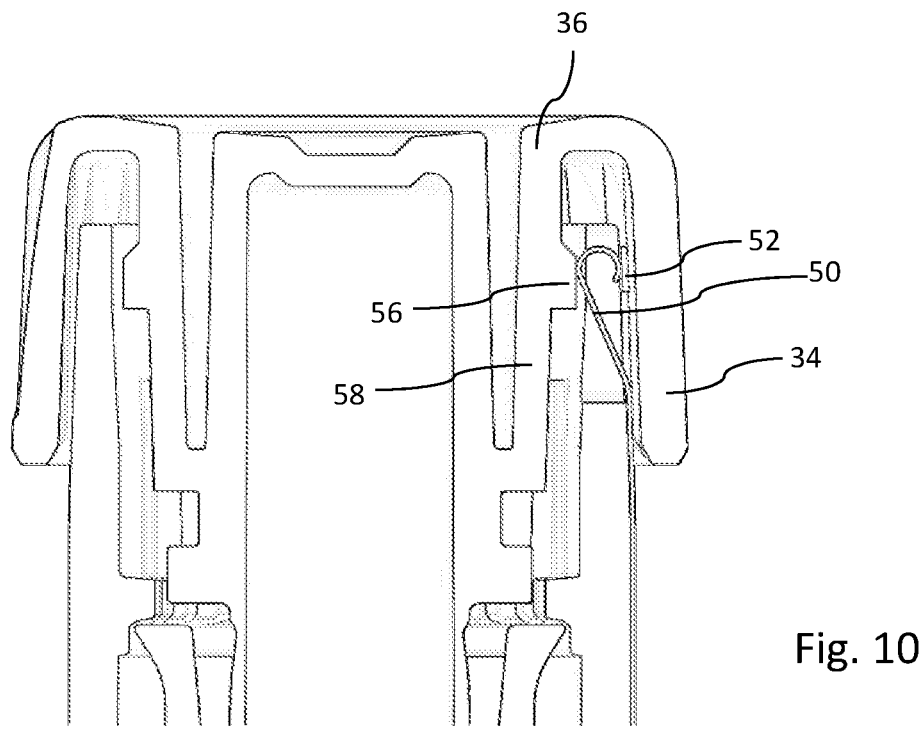
FIG. 10 shows another embodiment of a switch in a first configuration and FIG. 11 shows another, second configuration of the switch according to FIG. 10.
Figure 11:
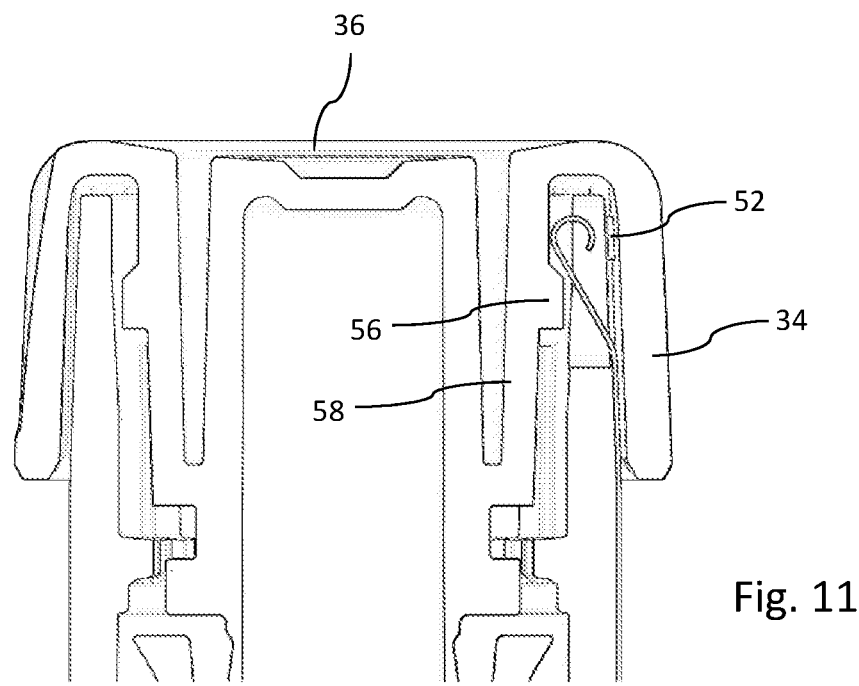

In still another embodiment, as shown in FIGS. 10 and 11, the conductive ring 52 is supported on an inside facing wall portion of the dose setting member 34 or dose dispensing member 36 while the contact members 50, 51 are biased radially outwardly by means of a radially outwardly extending protrusion 56 located on the inner sleeve portion 58 of the dose setting member 34. Also here, axially-directed displacement of the dose setting member 34 and hence of the radially outwardly extending protrusion 56 allows that the contact member 50 is displaced radially inwardly, thereby releasing from the conductive ring 52 as shown in FIG. 11.

Even though the embodiment according to FIGS. 10 and 11 is illustrated with only one contact member 50 it may be equally implemented with two diametrically oppositely disposed contact members 50, 51 as illustrated and explained with regard to FIGS. 3-9.

In another implementation the contact members 50, 51 may be coupled to the control 44 and/or to the accessory drive 26 in a different way so that only establishing of an electrical interconnection of the contact members 50, 51 leads to an activation of the accessory drive 26 in the dispensing mode of the drive mechanism 3. Accordingly, disconnecting of the contact members 50, 51 may then come along with a deactivation of the accessory drive 26.

The invention claimed is:

1. A drive mechanism of a drug delivery device for setting and dispensing of a dose of a medicament, the drive mechanism comprising:
   an elongated housing extending in an axial direction,
   a piston rod to operably engage with a piston of a cartridge containing the medicament, and
   an accessory drive operably engaged with the piston rod to support a manually operated dose dispensing displacement of the piston rod,
   wherein the accessory drive is electrically driven,
   wherein the accessory drive is coupled with a switch to selectively activate and/or deactivate the accessory drive, and
   wherein the switch is actuatable against a restoring force.

2. The drive mechanism according to claim 1, comprising a dosing arrangement being at least one of manually or axially displaceable relative to the housing, the dosing arrangement for setting and/or dispensing of the dose.

3. The drive mechanism according to claim 2, wherein the dosing arrangement is axially displaceable in a proximal direction relative to the housing for setting of the dose.

4. The drive mechanism of claim 2, wherein the dosing arrangement comprises a dose setting member, a dose indicating member and a dose dispensing member.

5. The drive mechanism according to claim 4, wherein the switch is operably engaged with the dose dispensing member or wherein the switch is integrated into the dose dispensing member.

6. The drive mechanism according to claim 4, wherein the switch is located in an interface between the dose dispensing member and the dose setting member and/or in an interface between the dose dispensing member and the dose indicating member.

7. The drive mechanism according to claim 4, wherein the accessory drive is operably engageable with the dose setting member or with the dose indicating member during a dose dispensing procedure for dispensing of the dose.

8. The drive mechanism according to claim 4, wherein the dose dispensing member is operably engaged with the piston rod during dose dispensing.

9. The drive mechanism according to claim 1, wherein the switch is operable to quantitatively determine a dispensing force acting thereon in a distal direction during dose dispensing.

10. The drive mechanism according to claim 1, further comprising a control to regulate a power of the accessory drive in dependence of an applied dispensing force.

11. The drive mechanism according to claim 1, wherein the switch is operable to quantitatively determine a size or magnitude of a dispensing force acting thereon in a distal direction during does dispensing.

12. The drive mechanism according to claim 11, wherein a power of the accessory drive is controlled or regulated by the control in accordance of the dispensing force.

13. The drive mechanism according to claim 1, wherein the switch comprises a load cell or at least one pressure sensitive member allowing to measure or to determine a magnitude of a force exerted by a user onto the switch.

14. The drive mechanism according to claim 1, wherein the accessory drive is configured to provide a force or torque transferred to the piston rod for driving the piston rod in a distal direction.

15. A drug delivery device for setting and dispensing of a dose of a medicament, the device comprising a cartridge and a drive mechanism, the drive mechanism comprising:
an elongated housing extending in an axial direction,
a piston rod to operably engage with a piston of a cartridge containing the medicament, and
an accessory drive operably engaged with the piston rod to support a manually operated dose dispensing displacement of the piston rod,
wherein the accessory drive is electrically driven,
wherein the accessory drive is coupled with a switch to selectively activate and/or deactivate the accessory drive,
wherein the switch is actuatable against a restoring force, and
wherein the cartridge is operably engaged with the piston rod.

16. A drive mechanism of a drug delivery device for setting and dispensing of a dose of a medicament, the drive mechanism comprising:
an elongated housing extending in an axial direction,
a piston rod to operably engage with a piston of a cartridge containing the medicament, and
an accessory drive operably engaged with the piston rod to support a manually operated dose dispensing displacement of the piston rod,
wherein the accessory drive is electrically driven,
wherein the accessory drive is coupled with a switch to selectively activate and/or deactivate the accessory drive, and
wherein the switch comprises a load cell or at least one pressure sensitive member allowing to measure or to determine a magnitude of a force exerted by a user onto the switch.

17. A drug delivery device for setting and dispensing of a dose of a medicament, the drug delivery device comprising a cartridge and a drive mechanism, the drive mechanism comprising:
an elongated housing extending in an axial direction,
a piston rod to operably engage with a piston of a cartridge containing the medicament, and
an accessory drive operably engaged with the piston rod to support a manually operated dose dispensing displacement of the piston rod,
wherein the accessory drive is electrically driven,
wherein the accessory drive is coupled with a switch to selectively activate and/or deactivate the accessory drive,
wherein the switch comprises a load cell or at least one pressure sensitive member allowing to measure or to determine a magnitude of a force exerted by a user onto the switch, and
wherein the cartridge is operably engaged with the piston rod.

* * * * *

UNITED STATES PATENT AND TRADEMARK OFFICE
CERTIFICATE OF CORRECTION

PATENT NO.         : 10,695,502 B2                                                            Page 1 of 1
APPLICATION NO.    : 16/168788
DATED              : June 30, 2020
INVENTOR(S)        : Paul Richard Draper, Anthony Paul Morris and Stephen Francis Gilmore It is certified that error appears in the above-identified patent and that said Letters Patent is hereby corrected as shown below:

In the Claims

In Column 15, Line 33, Claim 11, delete "does" and insert -- dose --

Signed and Sealed this
Sixth Day of October, 2020

Andrei Iancu
*Director of the United States Patent and Trademark Office*